United States Patent
Schulze zur Wiesche et al.

(10) Patent No.: US 8,808,674 B2
(45) Date of Patent: Aug. 19, 2014

(54) HAIR TREATMENT AGENTS COMPRISING SURFACTANT(S) AND PROTEOLIPID(S)

(75) Inventors: Erik Schulze zur Wiesche, Hamburg (DE); Monika Noll, Norderstedt (DE); Elisabeth Poppe, Hamburg (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

(21) Appl. No.: 13/438,108

(22) Filed: Apr. 3, 2012

(65) Prior Publication Data
US 2012/0189570 A1    Jul. 26, 2012

Related U.S. Application Data

(63) Continuation of application No. PCT/EP2010/064232, filed on Sep. 27, 2010.

(30) Foreign Application Priority Data

Oct. 5, 2009  (DE) .......................... 10 2009 048 299

(51) Int. Cl.
*A61K 8/00*  (2006.01)
(52) U.S. Cl.
USPC ..................................... 424/70.1
(58) Field of Classification Search
None
See application file for complete search history.

(56) References Cited

U.S. PATENT DOCUMENTS

| 4,140,759 | A |  | 2/1979 | Mausner |
| 4,792,571 | A |  | 12/1988 | Schiltz et al. |
| 2004/0120918 | A1 |  | 6/2004 | Lintner et al. |
| 2007/0148118 | A1 |  | 6/2007 | Montanari et al. |
| 2007/0207111 | A1 | * | 9/2007 | Nomura et al. ............ 424/70.14 |
| 2009/0111750 | A1 | * | 4/2009 | Kelly et al. ...................... 514/12 |
| 2011/0274640 | A1 | * | 11/2011 | Schulze Zur Wiesche et al. ........................ 424/70.13 |

FOREIGN PATENT DOCUMENTS

| DE | 3725030 A1 |  | 2/1989 |
| GB | 1425939 A | * | 4/1976 |
| WO | WO 92/13829 A1 |  | 8/1992 |

OTHER PUBLICATIONS

PCT International Search Report (PCT/EP2010/064232) dated Feb. 15, 2013.
Schoenberg; "Conditioners from Natural Lipids"; SOFW: Seifen, Oele, Fette, Wachse Journal; vol. 117; No. 17; pp. 657-659; 1991.

* cited by examiner

*Primary Examiner* — Paul Dickinson
(74) *Attorney, Agent, or Firm* — David K. Benson

(57) ABSTRACT

The present invention is a hair treatment agent comprising at least one surfactant and at least one proteolipid of the formula R'—X—R", wherein R' is a straight-chain or branched, saturated or unsaturated hydrocarbon radical having 11 to 24 carbon atoms; R" is a protein, a peptide, or a protein hydrolyzate; X is —C(O)O—, —N$^+$(R$^{III}_2$)R$^{IV}$—, or —N(R$^{III}$)R$^{IV}$—; R$^{III}$ is —(CH$_2$)$_x$—CH$_3$— with x=0-22; and R$^{IV}$ is —CH$_2$—CH(OH)—CH$_2$— or —(CH$_2$)$_x$— with x=0-22; with the proviso that R" consists of keratin or a keratin hydrolyzate when X is —C(O)O—. The agents of the present invention improve many properties of hair such as giving enhanced shine and impregnation of hair.

18 Claims, No Drawings

HAIR TREATMENT AGENTS COMPRISING SURFACTANT(S) AND PROTEOLIPID(S)

CROSS-REFERENCE TO RELATED APPLICATIONS

This application is a continuation of PCT Application Ser. No. PCT/EP2010/064232, filed on Sep. 27, 2010, which claims priority under 35 U.S.C. §119 to 10 2009 048 299.7 (DE) filed on Oct. 5, 2009. The disclosures PCT/EP2010/064232 and DE 10 2009 048 299.7 are hereby incorporated by reference in their entirety.

FIELD OF THE INVENTION

The present invention generally relates to hair treatment agents and in particular to hair treatment agents comprising surfactant and proteolipid and to the use of said agents for the cleaning and/or care of hair.

BACKGROUND OF THE INVENTION

Care agents for keratinic fibers are used to affect the natural structure and the properties of hair. Such treatments may be used to improve the ability to comb through both wet and dry hair, or used to increase fullness. Certain hair treatments may be used to protect the hair from increased split ends. For a long time, the common practice is to subject the hair to a specialized after-treatment. This involves treating the hair with special active substances, for example quaternary ammonium salts or special polymers, usually in the form of a rinse. As a result of this treatment, and depending on the formulations used, the ability to comb through the hair, the hair hold, and the fullness may be improved, as well as a reduction in the rate of split ends.

The known active substances cannot cover all the requirements to a sufficient extent, however. A need still exists for new active substances and/or novel combinations of active substances that give cosmetic agents good care properties and good biodegradability. In formulations containing surfactants and/or electrolytes in particular, there is a need for additional active care substances that can be readily incorporated into known formulations and not weakened in activity as a result of incompatibilities with other ingredients. Furthermore, other desirable features and characteristics of the present invention will become apparent from the subsequent detailed description of the invention and the appended claims, taken in conjunction with the accompanying drawings and this background of the invention.

BRIEF SUMMARY OF THE INVENTION

It has now been surprisingly found that significant improvements can be made to hair treatment agents if certain surfactant(s) and proteolipid(s) are incorporated therein.

In an exemplary embodiment of the present invention, a hair treatment agent comprises:
(a) at least one surfactant; and
(b) at least one proteolipid having the general formula (I), $$R'\text{—}X\text{—}R'' \qquad (I)$$

wherein R' is a straight-chain or branched, saturated or unsaturated hydrocarbon residue with 11 to 24 carbon atoms; R'' is a protein, a peptide, or a protein hydrolyzate; X is —C(O)O—, —N$^+$(R$^{III}_2$)R$^{IV}$—, or —N(R$^{III}$)R$^{IV}$—; R$^{III}$ is —(CH$_2$)$_x$—CH$_3$ with x=0-22; and R$^{IV}$ is —CH$_2$—, CH(OH)—CH$_2$—, or —(CH$_2$)$_x$— with x=0-22;

with the proviso that R'' is keratin or a keratin hydrolyzate when X is —C(O)O—.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

Hair treatment agents within the meaning of the present invention are, for example, hair shampoos, hair conditioners, conditioning shampoos, hairsprays, hair rinses, deep conditioners, hair masques, hair tonics, permanent wave fixing solutions, hair coloring shampoos, hair colorants, hair fixatives, hair-setting compositions, hairstyling preparations, blow-drying lotions, styling mousses, hair gels, hair waxes or combinations thereof. In view of the fact that men are often reluctant to use several different agents and/or several application steps, agents according to the invention are preferably those agents that a man may use in regular grooming. Preferred agents according to the invention are therefore shampoos, conditioning agents or hair tonics.

The agents according to the invention contain as a first essential ingredient at least one surfactant. Surfactants are surface-active substances that broadly include emulsifiers. The preferred surfactants for use in the present invention are selected from the group consisting of anionic surfactants, cationic surfactants, zwitterionic surfactants, ampholytic surfactants, nonionic surfactants, and mixtures thereof. Any of these preferred classes of surfactants is also understood to include surface-active substances that may be referred to as emulsifiers rather than surfactants.

Preferred hair treatment agents according to the invention comprises from 0.5 to 70 wt. %, more preferably 1 to 60 wt. %, and in particular 5 to 25 wt. %, of at least one anionic, nonionic, cationic, amphoteric surfactant, or mixtures thereof, based on the total weight of the hair treatment agent composition.

Suitable anionic surfactants and emulsifiers for the compositions according to the invention include any anionic surface-active substances suitable for use on the human body. Anionic surfactants are characterized by a water-solubilizing anionic group, such as a carboxylate, sulfate, sulfonate or phosphate group, and a lipophilic alkyl group with about 8 to 30 C atoms. In addition, glycol, polyglycol ether groups, ester, ether, amide, and hydroxyl groups can be contained in the molecule. Any of the suitable anionic surfactants and emulsifiers may be incorporated in the form of their corresponding sodium, potassium, ammonium, mono-, di-, and trialkanolammonium salts with 2 to 4 C atoms in the alkanol group.

Suitable anionic surfactants and emulsifiers for use in the present invention include, but are not limited to:
linear and branched fatty acids with 8 to 30 C atoms (soaps);
ether carboxylic acids of the formula R—O—(CH$_2$—CH$_2$O)$_x$—CH$_2$—COOH, in which R is a linear alkyl group with 8 to 30 C atoms and x=0 or 1 to 16;
acyl sarcosides with 8 to 24 C atoms in the acyl group;
acyl taurides with 8 to 24 C atoms in the acyl group;
acyl isethionates with 8 to 24 C atoms in the acyl group;
linear alkane sulfonates with 8 to 24 C atoms;
linear alpha-olefin sulfonates with 8 to 24 C atoms;
α-sulfo fatty acid methyl esters of fatty acids with 8 to 30 C atoms;

acyl glutamates of formula (I):

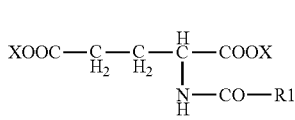
(I)

wherein R¹CO denotes a linear or branched acyl residue with 6 to 22 carbon atoms and 0, 1, 2 or 3 double bonds; and X denotes hydrogen, an alkali and/or alkaline earth metal, ammonium, alkylammonium, alkanolammonium or glucammonium, for example acyl glutamates, which are derived from fatty acids with 6 to 22, preferably 12 to 18 carbon atoms, such as for example $C_{12/14}$ or $C_{12/18}$ coconut fatty acid, lauric acid, myristic acid, palmitic acid and/or stearic acid, in particular sodium N-cocoyl and sodium N-stearoyl L-glutamate;
esters of a hydroxy-substituted di- or tricarboxylic acid of general formula (II):

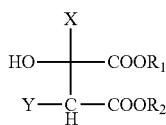
(II)

wherein X=H or a —CH$_2$COOR group, Y=H or —OH, on condition that Y=H when X=—CH$_2$COOR, R, R¹ and R², independently of one another, signify a hydrogen atom, an alkali or alkaline earth metal cation, an ammonium group, the cation of an ammonium organic base or a residue Z that originates from a polyhydroxylated organic compound, which are selected from the group of the etherified ($C_6$-$C_{18}$) alkyl polysaccharides with 1 to 6 monomeric saccharide units and/or the etherified aliphatic ($C_6$-$C_{16}$) hydroxyalkyl polyols with 2 to 16 hydroxyl residues, with the proviso that at least one of the groups R, R¹ or R² is a residue Z;
esters of sulfosuccinic acid or the sulfosuccinate of general formula (III):

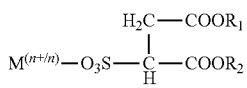
(III)

wherein $M^{(n+/n)}$ represents, for n=1, a hydrogen atom, an alkali metal cation, an ammonium group or the cation of an ammonium organic base and, for n=2, an alkaline earth metal cation; and R¹ and R² independently of one another signify a hydrogen atom, an alkali or alkaline earth metal cation, an ammonium group, the cation of an ammonium organic base or a residue Z that originates from a polyhydroxylated organic compound, which is selected from the group of the etherified ($C_6$-$C_{18}$) alkyl polysaccharides with 1 to 6 monomeric saccharide units and/or the etherified aliphatic ($C_6$-$C_{16}$) hydroxyalkyl polyols with 2 to 16 hydroxyl residues, with the proviso that at least one of the groups R¹ or R² is a residue Z;
sulfosuccinic acid mono- and dialkyl esters with 8 to 24 C atoms in the alkyl group and sulfosuccinic acid monoalkyl polyoxyethyl esters with 8 to 24 C atoms in the alkyl group and 1 to 6 oxyethyl groups;

alkyl sulfates and alkyl polyglycol ether sulfates of the formula R—(O—CH$_2$—CH$_2$)$_x$—OSO$_3$H, in which R is a preferably linear alkyl group with 8 to 30 C atoms and x=0 or 1-12;
mixed surface-active hydroxysulfonates such as those disclosed in DE-A-37 25 030 and incorporated herein by reference;
esters of tartaric acid and citric acid with alcohols, which represent addition products of about 2-15 molecules ethylene oxide and/or propylene oxide to $C_{8-22}$ fatty alcohols;
alkyl and/or alkenyl ether phosphates;
sulfated fatty acid alkylene glycol esters; and
monoglyceride sulfates and monoglyceride ether sulfates.

Preferred anionic surfactants and emulsifiers include acyl glutamates, acyl isethionates, acyl sarcosinates and acyl taurates, each having a linear or branched acyl residue with 6 to 22 carbon atoms and 0, 1, 2 or 3 double bonds, which is selected in particularly preferred embodiments from an octanoyl, decanoyl, lauroyl, myristoyl, palmitoyl and stearoyl residue, esters of tartaric acid, citric acid or succinic acid or the salts of these acids with alkylated glucose, in particular the products with the INCI name Disodium Coco-Glucoside Citrate, Sodium Coco-Glucoside Tartrate and Disodium Coco-Glucoside Sulfosuccinate, alkyl polyglycol ether sulfates and ether carboxylic acids with 8 to 18 C atoms in the alkyl group and up to 12 ethoxy groups in the molecule, sulfosuccinic acid mono and diallyl esters with 8 to 18 C atoms in the alkyl group and sulfosuccinic acid monoalkyl polyoxyethyl esters with 8 to 18 C atoms in the alkyl group and 1 to 6 ethoxy groups.

Those surface-active compounds carrying at least one quaternary ammonium group and at least one —COO$^{(-)}$ or —SO$_3^{(-)}$ group in the molecule are referred to as zwitterionic surfactants and emulsifiers. Particularly suitable zwitterionic surfactants and emulsifiers are the so-called betaines, such as the N-alkyl-N,N-dimethylammonium glycinates, for example cocoalkyl dimethylammonium glycinate, the N-acylaminopropyl-N,N-dimethylammonium glycinates, for example cocoacylaminopropyl dimethylammonium glycinate, and 2-alkyl-3-carboxymethyl-3-hydroxyethyl imidazolines each having 8 to 18 C atoms in the alkyl or acyl group and cocoacylaminoethyl hydroxyethyl carboxymethyl glycinate. A preferred zwitterionic surfactant is the fatty acid amide derivative known by the INCI name cocamidopropyl betaine.

More preferred anionic surfactants are alkyl sulfates, alkyl polyglycol ether sulfates and ether carboxylic acid salts with 10 to 18 C atoms in the alkyl group and up to 12 glycol ether groups in the molecule and sulfosuccinic acid mono- and dialkyl esters with 8 to 18 C atoms in the alkyl group and sulfosuccinic acid monoalkyl polyoxyethyl esters with 8 to 18 C atoms in the alkyl group and 1 to 6 oxyethyl groups.

Particularly preferred anionic surfactants are the alkali or ammonium salts of lauryl ether sulfate with a degree of ethoxylation of 2 to 4 EO.

Preferably, the hair treatment agents according to the invention comprise from 0.1 to 20 wt. %, preferably 0.25 to 17.5 wt. %, and in particular 5 to 15 wt. %, based on the total weight of the agent, a fatty alcohol ether sulfate of the formula:

wherein n denotes values of 5 to 21, preferably of 7 to 19, particularly preferably of 9 to 17 and in particular of 11 to 13; k denotes values of 1, 2, 3, 4, 5, 6, 7, 8, 9 or 10, preferably 1, 2 or 3 and in particular 2; and M denotes a cation from the group Na$^+$, K$^+$ NH$_4^+$, ½ Mg$^{2+}$, ½ Zn$^{2+}$, preferably Na$^+$.

The surface-active compounds carrying at least one quaternary ammonium group and at least one —COO$^{(-)}$ or —SO$_3^{(-)}$ group in the molecule are referred to as zwitterionic surfactants and emulsifiers. Particularly suitable zwitterionic surfactants and emulsifiers are the so-called betaines, such as the N-alkyl-N,N-dimethylammonium glycinates, for example cocoalkyl dimethylammonium glycinate, N-acylaminopropyl-N,N-dimethylammonium glycinates, for example cocoacylaminopropyl dimethylammonium glycinate, and 2-alkyl-3-carboxymethyl-3-hydroxyethyl imidazolines each with 8 to 18 C atoms in the alkyl or acyl group and cocoacylaminoethyl hydroxyethyl carboxymethyl glycinate. A preferred zwitterionic surfactant is the fatty acid amide derivative known by the INCI name cocamidopropyl betaine.

Ampholytic surfactants and emulsifiers are understood to be those surface-active compounds which, in addition to a $C_8$-$C_{24}$ alkyl or acyl group, contain at least one free amino group and at least one —COOH or —SO$_3$H group and are capable of forming internal salts. Examples of suitable ampholytic surfactants are N-alkylglycines, N-alkylaminopropionic acids, N-alkylaminobutyric acids, N-alkyliminodipropionic acids, N-hydroxyethyl-N-alkyl amidopropyl glycines, N-alkyl taurines, N-alkyl sarcosines, 2-alkylaminopropionic acids and alkylaminoacetic acids with in each case about 8 to 24 C atoms in the alkyl group. Particularly preferred ampholytic surfactants are N-cocoalkyl aminopropionate, cocoacylaminoethyl aminopropionate and $C_{12}$-$C_{18}$ acyl sarcosine.

Particularly preferred hair treatment agents according to the invention are characterized in that they contain amphoteric surfactant(s) from the groups of the N-alkylglycines, N-alkylpropionic acids, N-alkylaminobutyric acids, N-alkyliminodipropionic acids, N-hydroxyethyl-N-alkylamidopropylglycines, N-alkyl taurines, N-alkyl sarcosines, 2-alkylaminopropionic acids with in each case about 8 to 24 C atoms in the alkyl group, alkylaminoacetic acids with in each case about 8 to 24 C atoms in the alkyl group, N-cocoalkyl aminopropionate, cocoacylaminoethyl aminopropionates, $C_{12}$-$C_{18}$ acyl sarcosine, N-alkyl-N,N-dimethylammonium glycinates, for example cocoalkyl dimethylammonium glycinate, N-acylaminopropyl-N,N-dimethylammonium glycinates, for example cocoacylaminopropyl dimethylammonium glycinate, 2-alkyl-3-carboxymethyl-3-hydroxyethyl imidazolines each with 8 to 18 C atoms in the alkyl or acyl group, cocoacylaminoethyl hydroxyethyl carboxymethyl glycinate, the compounds known by the INCI name Cocamidopropyl Betaine and the compounds known by the INCI name Disodium Cocoamphodiacetate, with preferred agents containing the amphoteric surfactant(s) in quantities of 0.5 to 9 wt. %, preferably 0.75 to 8 wt. % and in particular 1 to 7.5 wt. %, based in each case on the total agent.

Particularly preferred hair treatment agents contain as amphoteric surfactants betaines of formula (VI):

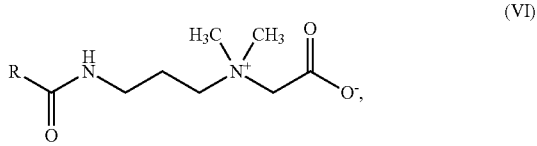

(VI)

wherein R denotes a straight-chained or branched, saturated or mono- or polyunsaturated alkyl or alkenyl residue with 8 to 24 carbon atoms.

These surfactants are referred to according to the INCI nomenclature as amidopropyl betaines, the representatives derived from coconut fatty acids being preferred and referred to as cocamidopropyl betaines. Particularly preferred surfactants having formula (VI) are selected from the group consisting of H$_3$C—(CH$_2$)$_7$—C(O)—NH—(CH$_2$)$_3$N$^+$(CH$_3$)$_2$CH$_2$COO$^-$, H$_3$C—(CH$_2$)$_9$—C(O)—NH—(CH$_2$)$_3$N$^+$(CH$_3$)$_2$CH$_2$COO$^-$, H$_3$C—(CH$_2$)$_{11}$—C(O)—NH—(CH$_2$)$_3$N$^+$(CH$_3$)$_2$ CH$_2$COO$^-$, H$_3$C—(CH$_2$)$_{13}$—C(O)—NH—(CH$_2$)$_3$N$^+$(CH$_3$)$_2$CH$_2$COO$^-$, H$_3$C—(CH$_2$)$_{15}$—C(O)—NH—(CH$_2$)$_3$ N$^+$(CH$_3$)$_2$CH$_2$COO$^-$, H$_3$C—(CH$_2$)$_7$—CH=CH—(CH$_2$)$_7$—C(O)—NH—(CH$_2$)$_3$N$^+$(CH$_3$)$_2$CH$_2$COO$^-$, and mixtures thereof.

Surfactants of formula (VI) are preferably incorporated in the agents of the present invention at from 0.25 to 8 wt. %, more preferably 0.5 to 7 wt. %, most preferably 0.75 to 6.5 wt. %, and in particular 1 to 5.5 wt. %, based on the total weight of the agent.

In addition to the ampho-surfactants of formula (VI), or instead of them, the hair treatment agents according to the invention can, with particular preference, contain as amphoteric surfactants betaines of formula (VII):

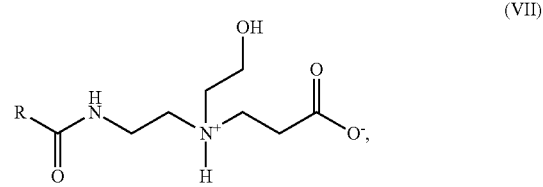

(VII)

wherein R denotes a straight-chained or branched, saturated or mono- or polyunsaturated alkyl or alkenyl residue with 8 to 24 carbon atoms.

These surfactants are known in accordance with the INCI nomenclature as amphoacetates, with the representatives derived from coconut fatty acids being preferred and being referred to as cocoamphoacetates.

For technical reasons relating to their manufacture, surfactants of this type always also contain betaines of formula (VIIa):

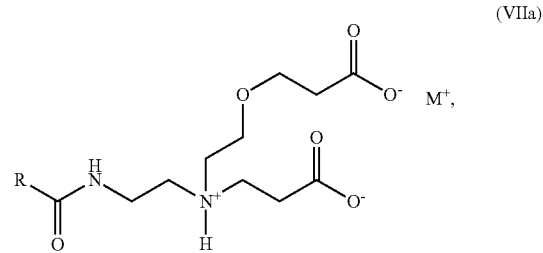

(VIIa)

wherein R denotes a straight-chained or branched, saturated or mono- or polyunsaturated alkyl or alkenyl residue with 8 to 24 carbon atoms and M denotes a cation.

These surfactants are referred to in accordance with the INCI nomenclature as amphodiacetates, with the representatives derived from coconut fatty acids being preferred and being referred to as cocoamphodiacetates.

Preferred surfactants having formula (VII) are chosen from the group of:
H$_3$C—(CH$_2$)$_7$—C(O)—NH—(CH$_2$)$_2$NH$^+$(CH$_2$CH$_2$OH) CH$_2$CH$_2$COO$^-$,
H$_3$C—(CH$_2$)$_9$—C(O)—NH—(CH$_2$)$_2$NH$^+$(CH$_2$CH$_2$OH) CH$_2$CH$_2$C COO$^-$, H₃C—(CH₂)₁₁C(O)—NH—(CH₂)₂NH⁺(CH₂CH₂OH)
    CH₂CH₂COO⁻,
H₃C—(CH₂)₁₃—C(O)—NH—(CH₂)₂NH⁺(CH₂CH₂OH)
    CH₂CH₂COO⁻,
H₃C—(CH₂)₁₅—C(O)—NH—(CH₂)₂NH⁺(CH₂CH₂OH)
    CH₂CH₂COO⁻,
H₃C—(CH₂)₇—CH=CH—(CH₂)₇—C(O)—NH—(CH₂)₂
    NH⁺(CH₂CH₂OH)CH₂CH₂COO⁻.

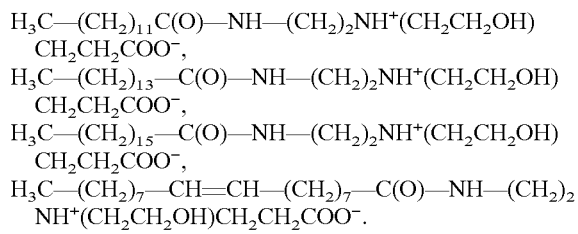

Surfactants of formula (VII) are preferably incorporated from 0.25 to 8 wt. %, more preferably 0.5 to 7 wt. %, most preferably 0.75 to 6.5 wt. %, and in particular 1 to 5.5 wt. %, based on the total weight of the treatment agent.

Particularly preferred nonionic surfactants are alkyl polyglycosides. Accordingly, hair treatment agents according to the invention are preferred which contain as nonionic surfactants—based on their weight—0.1 to 20 wt. % alkyl polyglycosides of the general formula RO—(Z)ₓ, wherein R denotes alkyl, Z denotes sugar and x denotes the number of sugar units.

Alkyl polyglycosides corresponding to the general formula RO—(Z)ₓ, wherein R denotes alkyl, Z denotes sugar and x denotes the number of sugar units, are preferably used according to the invention.

Particularly preferred are those alkyl polyglycosides in which R consists substantially of C₈ and C₁₀ alkyl groups; C₁₂ and C₁₄ alkyl groups; C₈ to C₁₆ alkyl groups; C₁₂ to C₁₆ alkyl groups; or C₁₆ to C₁₈ alkyl groups.

It is possible to use any mono- or oligosaccharide for the sugar building block Z. Sugars with 5 or 6 carbon atoms and the corresponding oligosaccharides are generally used. Preferred sugar building blocks are glucose, fructose, galactose, arabinose and sucrose; glucose is particularly preferred.

The alkyl polyglycosides that find use according to the invention contain on average 1.1 to 5 sugar units. Alkyl polyglycosides with x values of 1.1 to 2.0 are preferred. Most particularly preferred are alkyl glycosides in which x is 1.1 to 1.8

Other surfactants that can be used particularly advantageously in the agents according to the invention—in particular in a mixture with alkyl polyglycosides—are glutamates, aspartates and sulfoacetates. Hair treatment agents according to the invention are preferred here which contain—based on their weight—0.1 to 20 wt. % fatty acid glutamates (acyl glutamates) and/or fatty acid aspartates (acyl aspartates) and/or alkyl sulfoacetates (sulfoacetic acid alkyl esters).

Acyl glutamates can be described by the formula:

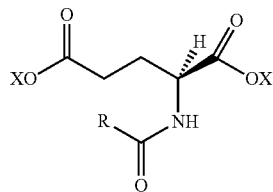

wherein R—CO denotes a linear or branched acyl residue with 6 to 22 carbon atoms and 0 and/or 1, 2 or 3 double bonds and X denotes hydrogen, an alkali and/or alkaline earth metal, ammonium, alkylammonium, alkanolammonium or glucammonium. Commercial products are available, for example, from Hoechst AG, Frankfurt/DE or Ajinomoto Co. Inc., Tokyo/JP.

Typical examples of suitable acyl glutamates are anionic surfactants that are derived from fatty acids with 6 to 22, preferably 12 to 18 carbon atoms, such as, for example, C12/14 or C12/18 coconut fatty acid, lauric acid, myristic acid, palmitic acid and/or stearic acid. Particularly preferred are sodium N-cocoyl and sodium N-stearoyl L-glutamate.

The agents according to the invention can contain the alkyl and/or alkenyl oligoglucosides and the acyl glutamates in a weight ratio of 1:99 to 99:1, preferably 10:90 to 90:10 and in particular 80:20 to 50:50.

Acyl aspartates can be described by the formula:

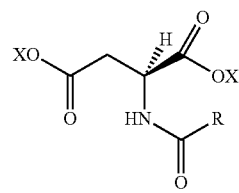

wherein R—CO denotes a linear or branched acyl residue with 6 to 22 carbon atoms and 0 and/or 1, 2 or 3 double bonds and X denotes hydrogen, an alkali and/or alkaline earth metal, ammonium, alkylammonium, alkanolammonium or glucammonium. Commercial products are available, for example, from Hoechst AG, Frankfurt/DE or Ajinomoto Co. Inc., Tokyo/JP.

Typical examples of suitable acyl aspartates are anionic surfactants that are derived from fatty acids with 6 to 22, preferably 12 to 18 carbon atoms, such as, for example, C12/14 or C12/18 coconut fatty acid, lauric acid, myristic acid, palmitic acid and/or stearic acid. Particularly preferred are sodium N-cocoyl and sodium N-stearoyl L-aspartate.

The agents according to the invention can contain the alkyl and/or alkenyl oligoglucosides and the acyl aspartates likewise in a weight ratio of 1:99 to 99:1, preferably 10:90 to 90:10 and in particular 80:20 to 50:50.

Sulfoacetates (sulfoacetic acid esters) are generally salts of esters of sulfoacetic acid and can be described by the general formula R—O—C(O)—CH₂—SO₂—OX, wherein R denotes a linear or branched alkyl or alkenyl residue with 6 to 22 carbon atoms and 0 and/or 1, 2 or 3 double bonds and X denotes hydrogen, an alkali and/or alkaline earth metal, ammonium, alkylammonium, alkanolammonium or glucammonium. Particularly preferred is the sodium salt of sulfoacetic acid having the INCI name Sodium Lauryl Sulfoacetate and chemical structure H₃C—(CH₂)₁₁—O—CO—CH₂—SO₂—ONa.

Sodium lauryl sulfoacetate is a white, free-flowing powder which has a neutral reaction, with good foaming properties, wetting properties and dispersing properties.

It is possible according to the invention to use cationic surfactants such as quaternary ammonium compounds, the esterquats and the amidoamines. Hair cleaning agents according to the invention that are particularly preferred are characterized in that they contain as cationic care substance—based on their weight—0.05 to 7.5 wt. %, preferably 0.1 to 5 wt. %, particularly preferably 0.2 to 3.5 wt. % and in particular 0.25 to 2.5 wt. % cationic surfactant(s) from the group of the quaternary ammonium compounds and/or the esterquats and/or the amidoamines, preferred cationic surfactant(s) being selected from alkyltrimethylammonium chlorides with preferably 10 to 18 carbon atoms in the alkyl residue and/or dialkyldimethylammonium chlorides with preferably 10 to 18 carbon atoms in the alkyl residue and/or trialkylmethylammonium chlorides with preferably 10 to 18 carbon atoms in the alkyl residue and/or cetyltrimethylammonium chloride and/or stearyltrimethylammonium chloride and/or distearyldimethylammonium chloride and/or lauryldimethylammonium chloride and/or lauryldimethylbenzylammonium chloride and/or tricetylmethylammonium chloride and/or Quatemium-27 and/or Quaternium-83 and/or N-methyl-N(2-hydroxyethyl)-N,N-(ditallow acyloxyethyl) ammonium methosulfate and/or N-methyl-N(2-hydroxyethyl)-N,N-(distearoyloxyethyl)ammonium methosulfate and/or N,N-dimethyl-N,N-distearoyloxyethylammonium chloride and/or N,N-di(2-hydroxyethyl)-N,N-(fatty acid ester ethyl)ammonium chloride.

As the second essential ingredient, the agents of the present invention also comprise at least one proteolipid corresponding to the general formula (I), $$R'\text{---}X\text{---}R'' \qquad (I)$$

wherein R' denotes a straight-chained or branched, saturated or unsaturated hydrocarbon residue with 11 to 24 carbon atoms; R'' denotes a protein, a peptide, or a protein hydrolyzate; X denotes —C(O)O—, —N$^+$(R$^{III}_2$)R$^{IV}$—, or —N(R$^{III}$R$^{IV}$—; R$^{III}$ denotes —(CH$_2$)$_x$—CH$_3$ with x=0-22; and R$^{IV}$ denotes —CH$_2$—, CH(OH)—CH$_2$—, or —(CH$_2$)$_x$— with x=0-22; with the proviso that R'' is keratin or a keratin hydrolyzate when X is —C(O)O—.

The proteolipids are preferably used within certain quantities in the agents according to the invention. Preferred hair treatment agents according to the invention contain—based on their weight—0.01 to 10 wt. %, preferably 0.02 to 5 wt. %, particularly preferably 0.05 to 2.5 wt. %, more preferably 0.1 to 1 wt. % and in particular 0.15 to 0.5 wt. % proteolipid(s).

The residue R'' in formula (I) denotes a peptide, a protein, or a protein hydrolyzate. When X=—C(O)O—, R'' is selected from the group of keratin or keratin hydrolyzate.

Preferred residues R'' are oligopeptides having at least one amino acid sequence Glu-Glu-Glu:

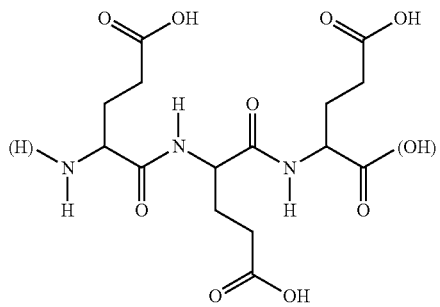

wherein the amino group can be present in free or protonated form and the carboxy groups can be present in free or deprotonated form.

In this, as in all of the formulae below, the bracketed hydrogen atom of the amino group, like the bracketed hydroxy group of the acid function, means that the groups concerned may be present as such (in which case it is an oligopeptide with the respective number of amino acids as illustrated (in formula 3 above)) or that the amino acid sequence is present in an oligopeptide which also comprises other amino acids—depending on where the other amino acid(s) is/are bound, the bracketed components in the above formula are replaced by the other amino acid residue(s).

Oligopeptides within the meaning of the present application are condensation products of amino acids linked by peptide bonds in the manner of an acid amide, comprising at least 3 and no more than 25 amino acids.

In preferred hair treatment agents according to the invention of the embodiment described above, the oligopeptide (=the residue R'') comprises 5 to 15 amino acids, preferably 6 to 13 amino acids, particularly preferably 7 to 12 amino acids and in particular 8, 9 or 10 amino acids.

Depending on whether other amino acids are bound to the sequence Glu-Glu-Glu and on the nature of these amino acids, and as a function of the selection of the residues R' and optionally R$^{III}$ and R$^{IV}$, the molecular weight of the proteolipid contained in the agents according to the invention can vary. Preferred hair treatment agents according to the invention are characterized in that the proteolipid has a molecular weight of 1,000 to 30,000 Dalton, preferably of 1,250 to 25,000 Dalton, particularly preferably of 1,500 to 20,000 Dalton, and in particular 2,000 to 15,000 Dalton.

The preferred oligopeptide residue R'' comprises other amino acids bound to the three glutamic acid sequence. These other amino acids are preferably selected from certain amino acids, while certain other representatives are less preferred according to the invention.

Thus it is preferred if the residue R'' of the proteolipids used in the agents according to the invention contains no methionine. It is more preferred if the residue R'' of the proteolipids used in the agents according to the invention contains no cysteine and/or cystine.

It is more preferred if the residue R'' of the proteolipids used in the agents according to the invention contains no aspartic acid and/or asparagine. It is more preferred if the residue R'' of the proteolipids used in the agents according to the invention contains no serine and/or threonine.

In contrast, it is preferred if the residue R'' of the proteolipids used in the agents according to the invention contains tyrosine. It is more preferred if the residue R'' of the proteolipids used in the agents according to the invention contains leucine. It is more preferred if the residue R'' of the proteolipids used in the agents according to the invention contains isoleucine. It is more preferred if the residue R'' of the proteolipids used in the agents according to the invention contains arginine. It is more preferred if the residue R'' of the proteolipids used in the agents according to the invention contains valine.

Oligopeptides that are particularly preferred as residue R'' and amino acid sequences contained in the preferred oligopeptides are described below.

A particularly preferred oligopeptide additionally contains tyrosine, which is preferably bound by its acid function to the Glu-Glu-Glu sequence. Preferred hair treatment agents according to the invention are therefore characterized in that the oligopeptide contained as residue R'' in the proteolipids of formula (I) has at least one amino acid sequence Tyr-Glu-Glu-Glu:

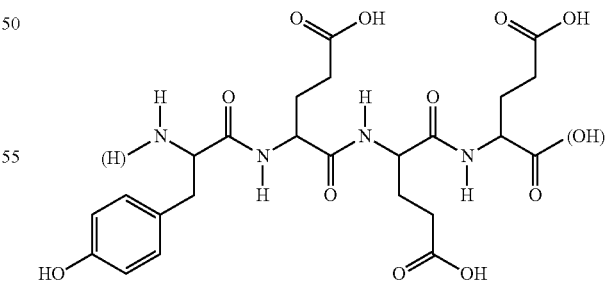

wherein the amino group can be present in free or protonated form and the carboxy groups can be present in free or deprotonated form.

Another particularly preferred oligopeptide additionally contains isoleucine, which is preferably bound by its amino function to the Glu-Glu-Glu sequence. Preferred hair treatment agents according to the invention are therefore characterized in that the oligopeptide contained as residue R" in the proteolipids of formula (I) has at least one amino acid sequence Glu-Glu-Glu-Ile:

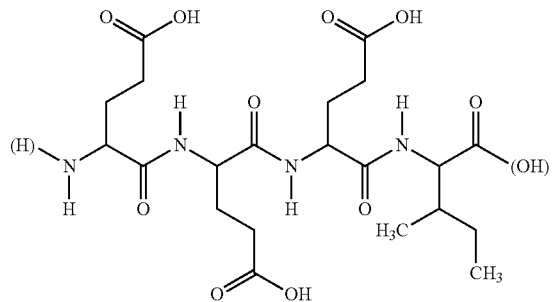

wherein the amino group can be present in free or protonated form and the carboxy groups can be present in free or deprotonated form Oligopeptides comprising both of the above-mentioned amino acids (tyrosine and isoleucine) are preferred according to the invention. Particularly preferred here are hair treatment agents according to the invention in which the oligopeptide contained as residue R" in the proteolipids of formula (I) has at least one amino acid sequence Tyr-Glu-Glu-Glu-Ile:

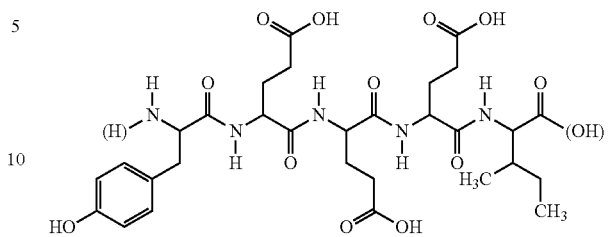

wherein the amino group can be present in free or protonated form and the carboxy groups can be present in free or deprotonated form.

More preferred oligopeptides additionally contain arginine, which is preferably present bound to isoleucine. Preferred hair treatment agents according to the invention are therefore characterized in that the oligopeptide contained as residue R" in the proteolipids of formula (I) has at least one amino acid sequence Tyr-Glu-Glu-Glu-Ile-Arg:

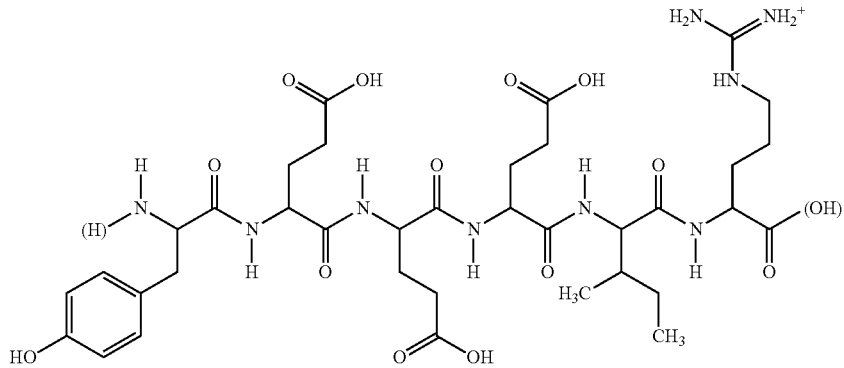

wherein the amino groups can be present in free or protonated form and the carboxy groups can be present in free or deprotonated form.

Even more preferred oligopeptides additionally contain valine, which is preferably present bound to arginine. More preferred hair treatment agents according to the invention are therefore characterized in that the oligopeptide contained as residue R" in the proteolipids of formula (I) has at least one amino acid sequence Tyr-Glu-Glu-Glu-Ile-Arg-Val:

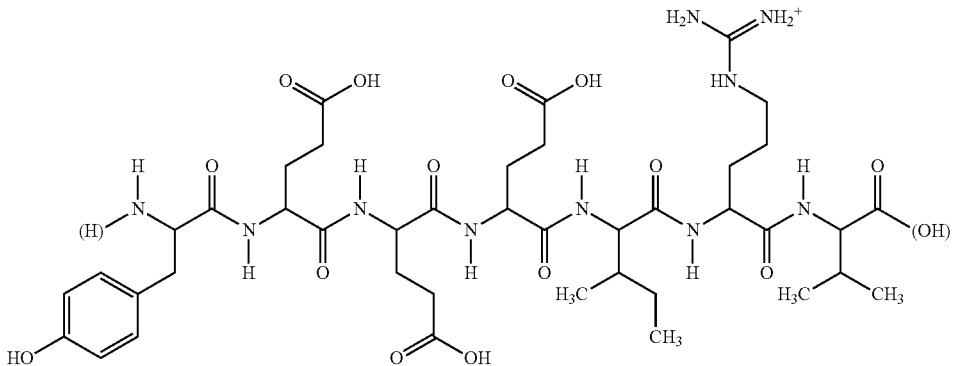

wherein the amino groups can be present in free or protonated form and the carboxy groups can be present in free or deprotonated form.

Even more preferred oligopeptides additionally contain leucine, which is preferably present bound to valine. More preferred hair treatment agents according to the invention are characterized in that the oligopeptide contained as residue R" in the proteolipids of formula (I) has at least one amino acid sequence Tyr-Glu-Glu-Glu-Ile-Arg-Val-Leu:

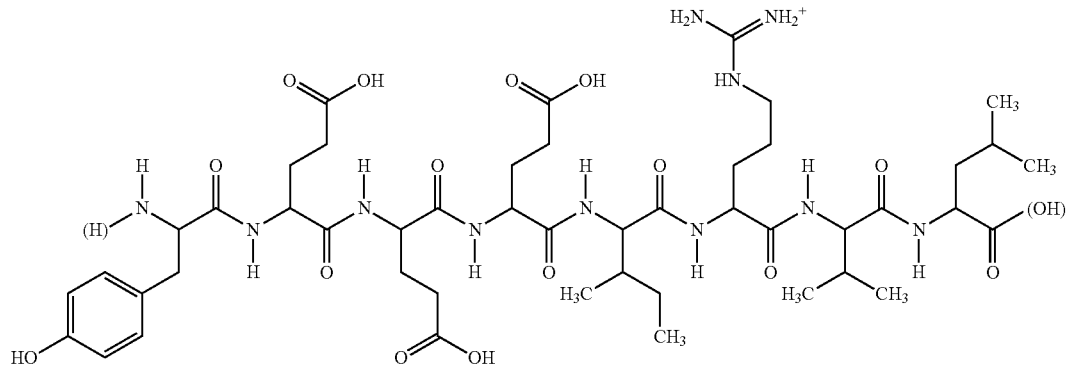

wherein the amino groups can be present in free or protonated form and the carboxy groups can be present in free or deprotonated form.

Particularly preferred oligopeptides additionally contain leucine, which is preferably present bound to tyrosine. More preferred hair treatment agents according to the invention are characterized in that the oligopeptide contained as residue R" in the proteolipids of formula (I) has at least one amino acid sequence Leu-Tyr-Glu-Glu-Glu-Ile-Arg-Val-Leu:

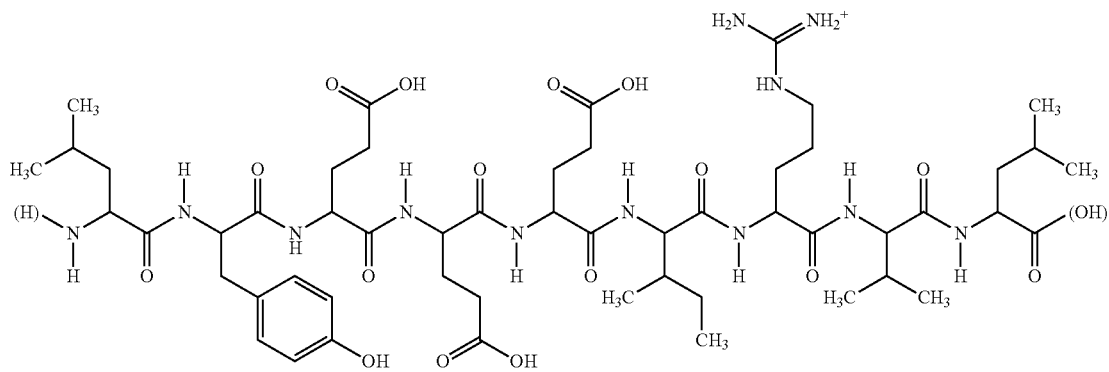

wherein the amino groups can be present in free or protonated form and the carboxy groups can be present in free or deprotonated form.

In summary, in particular hair treatment agents according to the invention are preferred which contain at least one proteolipid of formula (I), in which R" has at least one amino acid sequence Leu-Tyr-Glu-Glu-Glu-ILe-Arg-Val-Leu:

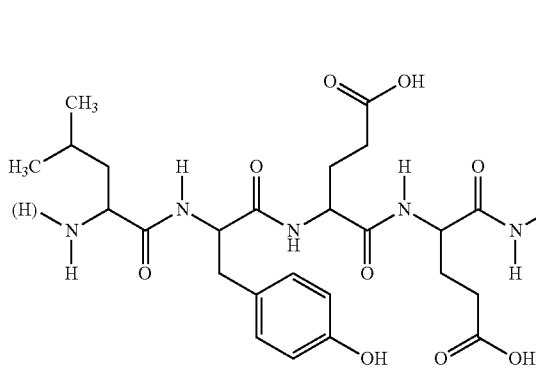 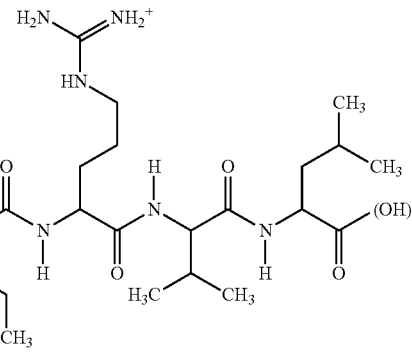

wherein the amino groups can be present in free or protonated faun and the carboxy groups can be present in free or deprotonated form.

As already mentioned, R" is selected from the group of keratin or keratin hydrolyzate when X in formula (I) is —C(O)O—.

In all other cases, the residue R" in formula (I) can denote a peptide or a protein or a protein hydrolyzate, with protein hydrolyzates being preferred. Protein hydrolyzates are product mixtures that are obtained by acid, base or enzyme catalyzed degradation of proteins. According to the invention, protein hydrolyzates of both plant and animal origin can be used.

Animal protein hydrolyzates are, for example, elastin, collagen, keratin, silk and milk protein hydrolyzates, which can also be present in the form of salts. Products of this type are marketed, for example, with the trade marks Dehylan® (Cognis), Promois® (Interorgana), Collapuron® (Cognis), Nutrilan® (Cognis), Gelita-Sol® (Deutsche Gelatine Fabriken Stoess & Co), Lexein® (Inolex) and Kerasol® (Croda).

The use of protein hydrolyzates of plant origin is preferred according to the invention, e.g. soybean, almond, rice, pea, potato and wheat protein hydrolyzates. Products of this type are available, for example, with the trade marks Gluadin® (Cognis), DiaMin® (Diamalt), Lexein® (Inolex) and Crotein® (Croda).

Preferably, regardless of the choice of the X in formula (I), the residue R" is selected from keratin or keratin hydrolyzates. Preferred hair treatment agents according to the invention are characterized in that they contain at least one proteolipid of formula (I), in which R" denotes keratin or a keratin hydrolyzate.

Particularly preferred groupings R—X— are listed in the tables of the priority document DE 102009048299.7, which is incorporated herein by reference. The groupings disclosed there are bound to keratin or keratin hydrolyzate as group R" in still more preferred embodiments of the present invention.

Regardless of the choice of the grouping —X— in formula (I), hair treatment agents according to the invention are preferred which contain at least one proteolipid of formula (I), in which $R^{III}$ signifies —$CH_3$ and $R^{IV}$ denotes —$(CH_2)_x$— with x=0, 1, 2, 3, 4, 5, 6, 7, 8.

Moreover, particularly preferred hair treatment agents according to the invention are characterized in that they contain at least one proteolipid of formula (I), in which X denotes —$N^+(CH_3)_2$—$CH_2$—CH(OH)—$CH_2$— and R' denotes —$(CH_2)_{17}$—$CH_3$.

Likewise, more preferred hair treatment agents according to the invention are characterized in that they contain at least one proteolipid of formula (I), in which X denotes —C(O)O— and R' denotes —$(CH_2)_{17}$—$CH_3$.

It has proved advantageous to use protein hydrolyzates as a third ingredient, in addition to the protein hydrolyzate that may be present in the proteolipids used according to the invention. These additional protein hydrolyzates enhance the action of the proteolipids and are in turn enhanced in their effects. The protein hydrolyzates were described in detail above as residue R". In summary, hair treatment agents according to the invention are preferred which additionally contain—based on their weight—0.01 to 10 wt. %, preferably 0.05 to 7 wt. %, particularly preferably 0.1 to 5 wt. %, more preferably 0.25 to 2.5 wt. % and in particular 0.5 to 2.0 wt. % protein hydrolyzate(s), preferably keratin hydrolyzate(s).

The care effects of the agents according to the invention can be enhanced still further by including certain care substances in the agent composition. These substances are preferably selected from certain groups of care substances that are known per se to harmonize extremely well with the proteolipids used according to the invention in terms of technical formulation and care effect.

It is preferred that the present hair treatment agents comprise a care substance selected from the group consisting of L-carnitine and/or salts thereof, panthenol and/or pantothenic acid, 2-furanones and/or derivatives thereof, (in particular pantolactone), taurine and/or salts thereof, niacinamide, ubiquinone, ectoine, allantoin, and mixtures thereof. Any of these care substances may be present at from 0.001 to 10 wt. %, preferably 0.005 to 7.5 wt. %, particularly preferably 0.01 to 5 wt. %, and in particular 0.05 to 2.5 wt. %, based on the total weight of the hair treatment agent.

In hair treatment agents of this embodiment according to the invention, the surfactant/proteolipid combination is combined with at least one care substance, which is selected from L-carnitine and/or salts thereof, panthenol and/or pantothenic acid, 2-furanones and/or derivatives thereof, in particular pantolactone, taurine and/or salts thereof, niacinamide, ubiquinones, ectoine, allantoin, and mixtures thereof. These care substances are described below.

As a betaine, L-carnitine can form addition compounds and double salts. Preferred L-carnitine derivatives according to the invention are in particular selected from acetyl L-carnitine, L-carnitine fumarate, L-carnitine citrate, lauroyl L-carnitine and particularly preferably L-carnitine tartrate. The above-mentioned L-carnitine compounds are available, for example, from Lonza GmbH (Wuppertal, Germany).

Preferred hair treatment agents according to the invention are characterized in that they contain—based on their weight—0.001 to 10 wt. %, preferably 0.005 to 7.5 wt. %, particularly preferably 0.01 to 5 wt. % and in particular 0.05 to 2.5 wt. % L-carnitine or L-carnitine derivatives, with preferred L-carnitine derivatives being selected from acetyl L-carnitine, L-carnitine fumarate, L-carnitine citrate, lauroyl L-carnitine and in particular L-carnitine tartrate.

Panthenol (IUPAC name: (2R)-2,4-dihydroxy-N-(3-hydroxypropyl)-3,3-dimethylbutanamide) is converted in the body to pantothenic acid. Pantothenic acid is a vitamin from the group of the B vitamins (vitamin $B_5$).

Preferred hair treatment agents according to the invention are characterized in that they contain—based on their weight—0.01 to 5 wt. %, preferably 0.05 to 2.5 wt. %, particularly preferably 0.1 to 1.5 wt. % and in particular 0.25 to 1 wt. % panthenol ((±)-2,4-dihydroxy-N-(3-hydroxypropyl)-3,3-dimethylbutyramide).

Preferred hair treatment agents according to the invention contain—based on their weight—0.01 to 15 wt. %, preferably 0.025 to 12.5 wt. %, particularly preferably 0.05 to 10 wt. %, more preferably 0.1 to 7.5 wt. % and in particular 0.5 to 5 wt. % of at least one of the following furanone derivatives: (R)-(−)-4-hydroxymethyl-γ-butyrolactone and/or D,L-4-hydroxymethyl-γ-butyrolactone and/or (S)-(+)-4-hydroxymethyl-γ-butyrolactone and/or R-(+2-hydroxy-3,3-dimethyl-γ-butyrolactone and/or D,L-2-hydroxy-3,3-dimethyl-γ-butyrolactone and/or S(+)-2-hydroxy-3,3-dimethyl-γ-butyrolactone and/or 4-hydroxy-2,5-dimethyl-3(2H)-furanone and/or tetrahydro-5-oxo-2-furancarboxylic acid and/or tetrahydro-5-oxo-2-furancarboxylic acid, Na salt, and/or tetrahydro-5-oxo-2-furancarboxylic acid, K salt, and/or 2,5-dihydro-5-methoxy-2-furanone and/or dihydro-3-hydroxy-4,4-dimethyl-2(3H)furanone. Other furanones are disclosed in the German priority document DE 102009048299.7, incorporated herein it its entirety.

In the most preferred embodiment of the present invention, dihydro-3-hydroxy-4,4-dimethyl-2(3H)-furanone (pantolactone) is used as the care substance.

Another care substance that possesses activating properties and is preferred for use herein is taurine. Preferred hair treatment agents according to the invention contain—based on their weight—0.01 to 15 wt. %, preferably 0.025 to 12.5 wt. %, particularly preferably 0.05 to 10 wt. %, more preferably 0.1 to 7.5 wt. % and in particular 0.5 to 5 wt. % taurine (2-aminoethanesulfonic acid).

Vitamins, provitamins, or vitamin precursors are another preferred group of care substance that may be included in the agents according to the invention. Vitamins for use herein may be selected from the group consisting of Vitamin A, $B_1$, $B_2$, $B_3$, $B_5$, $B_6$, C, E, F, H, and mixtures thereof.

The group of substances referred to as vitamin A includes retinol (vitamin $A_1$) and 3,4-didehydroretinol (vitamin $A_2$). β-Carotene is the provitamin of retinol. Suitable as vitamin A component according to the invention are, for example, vitamin A acid and esters thereof, vitamin A aldehyde and vitamin A alcohol and esters thereof, such as palmitate and acetate. The agents according to the invention contain the vitamin A component preferably in quantities of 0.05-1 wt. %, based on the total preparation.

The Vitamin B group includes Vitamin $B_1$ (thiamine), Vitamin $B_2$ (riboflavin), Vitamin $B_3$, Vitamin $B_5$, and Vitamin $B_6$. Often included are the compounds nicotinic acid and nicotinamide (niacinamide). Nicotinamide, which is contained in the agents used according to the invention preferably in quantities of 0.05 to 1 wt. %, based on the total agent, is preferred according to the invention.

Vitamin $B_5$ includes the compounds pantothenic acid, panthenol and pantolactone. In the context of this group, panthenol and/or pantolactone is preferably used (see below).

Derivatives of panthenol that can be used according to the invention are, in particular, the esters and ethers of panthenol as well as cationically derivatized panthenols. Individual representatives are, for example, panthenol triacetate, panthenol monoethyl ether and the monoacetate thereof as well as the cationic panthenol derivatives disclosed in WO 92/13829. The said compounds of the vitamin $B_5$ type are contained in the agents according to the invention preferably in quantities of 0.05-10 wt. %, based on the total agent. Quantities of 0.1-5 wt. % are particularly preferred.

Vitamin $B_6$ includes the compounds pyridoxine as well as pyridoxamine and pyridoxal.

Vitamin C (ascorbic acid) may be used in the agents according to the invention preferably in quantities of 0.1 to 3 wt. %, based on the total agent. Use in the form of the palmitic acid ester, the glucosides or phosphates may be preferred. Use in combination with tocopherols may likewise be preferred.

Vitamin E includes tocopherols, and in particular α-tocopherol. Tocopherol and its derivatives, including in particular the esters, such as the acetate, nicotinate, phosphate and succinate, may be included in the agents according to the invention preferably in quantities of 0.05-1 wt. %, based on the total agent.

The term "vitamin F" is usually understood to mean essential fatty acids, in particular linoleic acid, linolenic acid and arachidonic acid.

The compound (3aS,4S,6aR)-2-oxohexahydrothienol[3,4-d]-imidazole-4-valeric acid is referred to as vitamin H, but its trivial name biotin has now become accepted. Biotin is contained in the agents according to the invention preferably in quantities of 0.0001 to 1.0 wt. %, in particular in quantities of 0.001 to 0.01 wt. %.

In summary, hair treatment agents according to the invention are preferred which contain—based on their weight—0.1 to 5 wt. %, preferably 0.2 to 4 wt. %, particularly preferably 0.25 to 3.5 wt. %, more preferably 0.5 to 3 wt. % and in particular 0.5 to 2.5 wt. % vitamins and/or provitamins and/or vitamin precursors, which preferably belong to the groups A, B, C, E, F and H, with preferred agents containing -2,4-dihydroxy-N-(3-hydroxypropyl)-3,3-dimethylbutyramide, provitamin $B_5$) and/or pantothenic acid (vitamin $B_3$, vitamin $B_5$) and/or niacin, niacinamide or nicotinamide (vitamin $B_3$) and/or L-ascorbic acid (vitamin C) and/or thiamine (vitamin $B_1$) and/or riboflavin (vitamin $B_2$, vitamin G) and/or biotin (vitamin $B_7$, vitamin H) and/or folic acid (vitamin $B_9$, vitamin $B_c$ or vitamin M) and/or vitamin $B_6$ and/or vitamin $B_{12}$.

It has been shown that certain quinones possess a particular suitability as care substances. As another care substance, the agents according to the invention can therefore contain 0.0001 to 5 wt. % of at least one bio-quinone of the formula (Ubi):

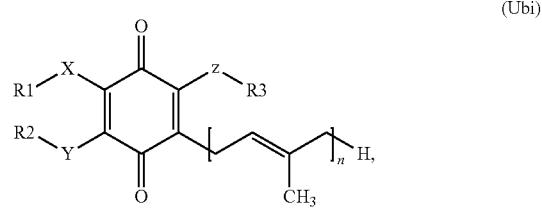

wherein X, Y, and Z independently of one another denote —O— or —NH— or $NR^4$ or a chemical bond; $R^1$, $R^2$, and $R^3$ independently of one another denote a hydrogen atom or an optionally substituted aryl group or an optionally substituted (C$_1$-C$_6$) alkyl group or a hydroxyalkyl group or a polyhydroxyalkyl group or an optionally substituted (C$_1$-C$_6$) alkylene group, or a (C$_1$-C$_6$) acyl residue, with preferred residues, independently of one another, being selected from —H, —CH$_3$, —CH$_2$CH$_3$, —(CH$_2$)$_2$CH$_3$, —CH(CH$_3$)$_2$, —(CH$_2$)$_3$CH$_3$, —CH(CH$_3$)CH$_2$CH$_3$, —CH$_2$CH(CH$_3$)$_2$, —C(CH$_3$)$_3$; R$^4$ denotes —CH$_3$, —CH$_2$CH$_3$, —(CH$_2$)$_2$CH$_3$, —CH(CH$_3$)$_2$, —(CH$_2$)$_3$CH$_3$, —CH(CH$_3$)CH$_2$CH$_3$, —CH$_2$CH(CH$_3$)$_2$, —C(CH$_3$)$_3$; and n denotes values of 1 to 20, preferably of 2 to 15, and in particular 5, 6, 7, 8, 9, 10.

Particularly preferred hair treatment agents according to the invention are characterized in that they contain as care substance—based on their weight—0.0001 to 1 wt. %, preferably 0.001 to 0.5 wt. % and particularly preferably 0.005 to 0.1 wt. % of at least one ubiquinone and/or of at least one ubiquinol and/or of at least one derivative of these substances, with preferred agents containing an ubiquinone of the formula (Ubi):

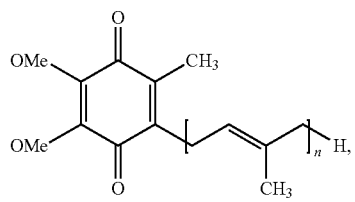

wherein n denotes the values=6, 7, 8, 9 or 10, particularly preferably 10 (coenzyme Q10).

Alternatively to the particularly preferred ubiquinones or in addition to them, the agents according to the invention can also contain plastoquinones. Here, preferred agents according to the invention are characterized in that they contain 0.0002 to 4 wt. %, preferably 0.0005 to 3 wt. %, particularly preferably 0.001 to 2 wt. %, more preferably 0.0015 to 1 and in particular 0.002 to 0.5 wt. % of at least one plastoquinone of the formula (Ubi-b):

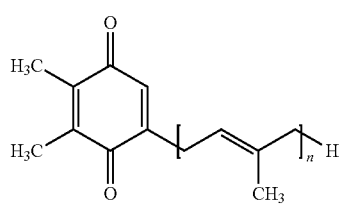

wherein n denotes values of 1 to 20, preferably of 2 to 15 and in particular 5, 6, 7, 8, 9, 10, with particularly preferred agents containing plastoquinone PQ-9.

As another care enhancer, the agents according to the invention can contain ectoine. Preferred hair treatment agents according to the invention are characterized in that they contain—based on their weight—0.001 to 10 wt. %, preferably 0.01 to 5 wt. %, particularly preferably 0.05 to 2.5 wt. % and in particular 0.1 to 1 wt. % (S)-2-methyl-1,4,5,6-tetrahydro-4-pyrimidinecarboxylic acid (ectoine) and the physiologically acceptable salts of this compound and/or (S,S)-5-hydroxy-2-methyl-1,4,5,6-tetrahydro-4-pyrimidinecarboxylic acid (hydroxyectoine) and the physiologically acceptable salts of this compound.

Another care substance is allantoin. Particularly preferred hair treatment agents according to the invention contain—based on their weight—0.001 to 10 wt. %, preferably 0.01 to 5 wt. %, particularly preferably 0.05 to 2.5 wt. % and in particular 0.1 to 1 wt. % 5-ureidohydantoin (allantoin).

To improve the elasticity and strengthen the internal structure of hair treated with agents according to the invention, the agents according to the invention can contain purine and/or purine derivatives as care substance. In particular, the combination of purine and/or purine derivatives with ubiquinones and/or plastoquinones as care substance leads to hair treated with corresponding agents displaying, inter alia, higher test values in differential thermal analysis and improved wet and dry combabilities.

Purine, the purines, and the purine derivatives, may be included as care substances from 0.001 to 2.5 wt. %, preferably 0.0025 to 1 wt. %, particularly preferably 0.005 to 0.5 wt. %, and in particular 0.01 to 0.1 wt. %, based on the total weight of the hair treatment agent. The preferred purine(s) and/or purine derivative(s) are chosen from the group consisting of purine, adenine, guanine, uric acid, hypoxanthine, 6-purinethiol, 6-thioguanine, xanthine, caffeine, theobromine, theophylline, and mixtures thereof.

It is furthermore advantageous to use purine or purine derivatives and bio-quinones in a particular ratio to one another. Here, agents according to the invention are preferred in which the weight ratio of purine (derivative(s)) to bio-quinone(s) is 10:1 to 1:100, preferably 5:1 to 1:50, particularly preferably 2:1 to 1:20, and in particular 1:1 to 1:10.

As already mentioned, caffeine is a particularly preferred purine derivative, and the coenzyme Q10 is a particularly preferred bio-quinone. Particularly preferred agents according to the invention are therefore characterized in that they contain—based on their weight—0.001 to 2.5 wt. %, preferably 0.0025 to 1 wt. %, particularly preferably 0.005 to 0.5 wt. % and in particular 0.01 to 0.1 wt. % caffeine and 0.0002 to 4 wt. %, preferably 0.0005 to 3 wt. %, particularly preferably 0.001 to 2 wt. %, more preferably 0.0015 to 1 and in particular 0.002 to 0.5 wt. % coenzyme Q10.

As care substance, the agents according to the invention can also contain flavonoids. Well over 6,500 different flavonoids are known, which can be divided into flavonols, flavones, flavanones, isoflavonoids and anthocyans.

According to the invention, flavonoids from all six groups can be used, with certain representatives from the individual groups being preferred as care substance owing to their particularly intensive action. Preferred flavonols are quercetin, rutin, kaempferol, myricetin and isorhamnetin, preferred flavanols are catechin, gallocatechin, epicatechin, epigallocatechin gallate, theaflavin and thearubigin, preferred flavones are luteolin, apigenin and morin, preferred flavanones are hesperetin, naringenin and eriodictyol, preferred isoflavonoids are genistein and daidzein, and preferred anthocyanidins (anthocyans) are cyanidin, delphinidin, malvidin, pelargonidin, peonidin and petunidin.

Particularly preferred hair treatment agents according to the invention are characterized in that they contain—based on their weight—0.001 to 2.5 wt. %, preferably 0.0025 to 1 wt. %, particularly preferably 0.005 to 0.5 wt. % and in particular 0.01 to 0.1 wt. % flavonoids, in particular flavonols, particularly preferably 3,3',4',5,7-pentahydroxyflavone (quercetin) and/or 3,3',4',5,7-pentahydroxyflavone-3-O-rutinoside (rutin).

The use of bisabolol and/or bisabolol oxides as care substance in the agents according to the invention is also preferred. Here, hair treatment agents according to the invention are preferred which additionally contain 0.001 to 5 wt. %, preferably 0.01 to 4 wt. %, particularly preferably 0.02 to 2.5 wt. % and in particular 0.1 to 1.5 wt. % bisabolol and/or oxides of bisabolol, preferably (−)-alpha-bisabolol.

Creatine is also suitable according to the invention as a care substance. Particularly preferred hair treatment agents according to the invention contain—based on their weight—0.01 to 15 wt. %, preferably 0.025 to 12.5 wt. %, particularly preferably 0.05 to 10 wt. %, more preferably 0.1 to 7.5 wt. % and in particular 0.5 to 5 wt. % N-methylguanidinoacetic acid (creatine).

The agents according to the invention can contain, in addition to the above-mentioned ingredients and other optional ingredients, other substances that prevent, alleviate or cure hair loss. In particular, a content of hair root stabilizing active substances is advantageous. These substances are described below.

Propecia (finasteride) is currently the only preparation approved worldwide with efficacy and acceptability proven in numerous studies. Propecia has the effect that less DHT is able to form from testosterone.

Minoxidil with or without supplementary additives, is probably the oldest hair growth agent with proven action. There are hair lotions that contain 2%-5% minoxidil, as well as gels with up to 15% minoxidil.

To combat hormonal influences on the hair follicles, spironolactone can be applied for external use in the form of a hair lotion and in combination with minoxidil. Spironolactones act as androgen receptor blockers, i.e. the binding of DHT to the hair follicles is prevented.

In summary, hair treatment agents according to the invention are preferred which additionally contain—based on their weight—0.001 to 5 wt. % hair root stabilizing substances, in particular minoxidil and/or finasteride and/or ketoconazole.

By means of additional active anti-dandruff substances (for example climbazole, piroctone olamine or zinc pyrithione), the quantity of the fungus that causes dandruff is reduced in a targeted manner, the microbial flora returns to the normal percentage composition and flaking is reduced to the physiological level. Laboratory tests have shown, however, that the different representatives of the *Pityrosporum ovale* species react differently to the active anti-dandruff substances. To combat all causes of dandruff to the maximum possible extent, therefore, a combination of active anti-dandruff substances is most successful.

In summary, hair treatment agents according to the invention are preferred which additionally contain—based on their weight—0.001 to 5 wt. % active anti-dandruff substances, in particular piroctone olamine (1-hydroxy-4-methyl-6-(2,4,4-trimethylpentyl)pyridin-2(1H)-one, compound with 2-aminoethanol, 1:1) and/or zinc pyrithione and/or selenium sulfide and/or climbazole and/or salicylic acid or fumaric acid.

In addition to the care substances, the agents according to the invention can contain further care substances. Their presence is not essential to achieve the effects according to the invention, but further effects, such as a pleasant handle or pleasant application feel can result from the use of these care substances.

As a further ingredient, the agents according to the invention can, with particular preference, contain one or more amino acids. Amino acids that can particularly preferably be used according to the invention come from the group glycine, alanine, valine, leucine, isoleucine, phenylalanine, tyrosine, tryptophan, proline, aspartic acid, glutamic acid, asparagine, glutamine, serine, threonine, cysteine, methionine, lysine, arginine, histidine, β-alanine, 4-aminobutyric acid (GABA), betaine, L-cystine (L-cyss), L-carnitine, L-citrulline, L-theanine, 3',4'-dihydroxy-L-phenylalanine (L-dopa), 5'-hydroxy-L-tryptophan, L-homocysteine, S-methyl-L-methionine, S-allyl-L-cysteine sulfoxide (L-alliin), L-trans-4hydroxyproline, L-5-oxoproline (L-pyroglutamic acid), L-phosphoserine, creatine, 3-methyl-L-histidine, L-ornithine, the use of both the individual amino acids and of mixtures being possible.

Preferred agents according to the invention contain one or more amino acids in relatively narrow quantitative ranges. Here, preferred hair treatment agents according to the invention are characterized in that they contain as care substance—based on their weight—0.01 to 5 wt. %, preferably 0.02 to 2.5 wt. %, particularly preferably 0.05 to 1.5 wt. %, more preferably 0.075 to 1 wt. % and in particular 0.1 to 0.25 wt. % amino acid(s), preferably from the group of glycine and/or alanine and/or valine and/or lysine and/or leucine and/or threonine.

As a further component, the agents according to the invention can contain at least one carbohydrate selected from the group consisting of monosaccharides, disaccharides, oligosaccharides, and mixtures thereof. The care substances may be present at from 0.01 to 5 wt. %, preferably 0.05 to 4.5 wt. %, particularly preferably 0.1 to 4 wt. %, more preferably 0.5 to 3.5 wt. % and in particular 0.75 to 2.5 wt. %, based on the total weight of the agent. The preferred carbohydrate(s) are selected from the group consisting of: monosaccharides, in particular D-ribose and/or D-xylose and/or L-arabinose and/or D-glucose and/or D-mannose and/or D-galactose and/or D-fructose and/or sorbose and/or L-fucose and/or L-rhamnose; disaccharides, in particular sucrose and/or maltose and/or lactose and/or trehalose and/or cellobiose and/or gentiobiose and/or isomaltose; and mixtures thereof.

Preferred agents according to the invention are characterized in that they contain at least one silicone. The silicone may be selected from the group consisting of (i) polyalkyl siloxanes, polyaryl siloxanes, polyalkyl aryl siloxanes, which are volatile or non-volatile, straight-chained, branched or cyclic, crosslinked or uncrosslinked, (ii) polysiloxanes, which contain in their general structure one or more organofunctional groups, which are selected from:
 a) substituted or unsubstituted aminated groups;
 b) (per)fluorinated groups;
 c) thiol groups;
 d) carboxylate groups;
 e) hydroxylated groups;
 f) alkoxylated groups;
 g) acyloxyalkyl groups;
 h) amphoteric groups;
 i) bisulfate groups;
 j) hydroxyacylamino groups;
 k) carboxy groups;
 l) sulfonic acid groups; and
 m) sulfate or thiosulfate groups, (iii) linear polysiloxane(A)-polyoxyalkylene(B) block copolymers of the type (A-B), with n>3, (iv) graft silicone polymers with an organic backbone containing no silicone, consisting of an organic main chain which is formed from organic monomers that contain no silicone, on which, in the chain and optionally on at least one end of the chain, at least one polysiloxane macromer has been grafted, (v) graft silicone polymers with a polysiloxane backbone, on which organic monomers that contain no silicone have been grafted, having a polysiloxane main chain, on which, in the chain and optionally on at least one end thereof, at least one organic macromer that contains no silicone has been grafted, and mixtures thereof.

Particularly preferred agents according to the invention contain the silicone(s) in quantities of 0.1 to 10 wt. %, preferably 0.25 to 7 wt. % and in particular 0.5 to 5 wt. %, based in each case on the total agent.

Particularly preferred silicones are represented by the formula $(CH_3)_3Si—[O—Si(CH_3)_2]_x—O—Si(CH_3)_3$, wherein x denotes a number from 0 to 100, preferably from 0 to 50, more preferably from 0 to 20 and in particular 0 to 10. The INCI nomenclature for this group of silicones is "dimethicones."

Preferred silicones that can be used according to the invention have viscosities from 0.2 to 2 mm$^2$s$^{-1}$ at 20° C., with silicones having viscosities of 0.5 to 1 mm$^2$s$^{-1}$ being particularly preferred.

Particularly preferred agents according to the invention contain one or more amino functional silicones. These silicones can be described e.g. by the formula:

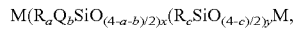

$$M(R_aQ_bSiO_{(4-a-b)/2})_x(R_cSiO_{(4-c)/2})_yM,$$

wherein R is a hydrocarbon or a hydrocarbon residue with 1 to about 6 carbon atoms, Q is a polar residue of the general formula —R$^1$HZ, wherein R$^1$ is a divalent bonding group, which is bound to hydrogen and to the residue Z, composed of carbon and hydrogen atoms, carbon, hydrogen and oxygen atoms or carbon, hydrogen and nitrogen atoms, and Z is an organic, amino functional residue, which contains at least one amino functional group; "a" assumes values in the range of about 0 to about 2, "b" assumes values in the range from about 1 to about 3, "a"+"b" is less than or equal to 3, and "c" is a number in the range from about 1 to about 3, and x is a number in the range from 1 to about 2,000, preferably from about 3 to about 50 and most preferably from about 3 to about 25, and y is a number in the range from about 20 to about 10,000, preferably from about 125 to about 10,000 and most preferably from about 150 to about 1,000, and M is a suitable silicone end group, as is known in the prior art, preferably trimethylsiloxy. Non-restrictive examples of the residues represented by R include alkyl residues, such as methyl, ethyl, propyl, isopropyl, isopropyl, butyl, isobutyl, amyl, isoamyl, hexyl, isohexyl and similar; alkenyl residues, such as vinyl, halovinyl, alkylvinyl, allyl, haloallyl, alkylallyl; cycloalkyl residues, such as cyclobutyl, cyclopentyl, cyclohexyl and similar; phenyl residues, benzyl residues, halogenated hydrocarbon residues, such as 3-chloropropyl, 4-bromobutyl, 3,3,3-trifluoropropyl, chlorocyclohexyl, bromophenyl, chlorophenyl and similar, and sulfurous residues, such as mercaptoethyl, mercaptopropyl, mercaptohexyl, mercaptophenyl and similar; R is preferably an alkyl residue containing 1 to about 6 carbon atoms, and R is most preferably methyl. Examples of R$^1$ include methylene, ethylene, propylene, hexamethylene, decamethylene, —CH$_2$CH(CH$_3$)CH$_2$—, phenylene, naphthylene, —CH$_2$CH$_2$SCH$_2$CH$_2$—, —CH$_2$CH$_2$OCH$_2$—, —OCH$_2$CH$_2$—, —OCH$_2$CH$_2$CH$_2$—, —CH$_2$CH(CH$_3$)C(O)OCH$_2$—, —(CH$_2$)$_3$CC(O)OCH$_2$CH$_2$—, —C$_6$H$_4$C$_6$H$_4$—, —C$_6$H$_4$—CH$_2$C$_6$H$_4$—, and —(CH$_2$)$_3$C(O)SCH$_2$CH$_2$—.

Z is an organic, amino functional residue, containing at least one functional amino group. One possible formula for Z is NH(CH$_2$)$_n$NH$_2$, wherein z is 1 or more. Another possible formula for Z is —NH(CH$_2$)$_z$(CH$_2$)$_{zz}$NH, wherein both z and zz are independently 1 or more, this structure comprising diamino ring structures, such as piperazinyl. Z is most preferably an —NHCH$_2$CH$_2$NH$_2$— residue. Another possible formula for Z is —N(CH$_2$)$_z$(CH$_2$)$_{zz}$NX$_2$ or —NX$_2$, wherein each X of X$_2$ is independently selected from the group consisting of hydrogen and alkyl groups with 1 to 12 carbon atoms, and zz is 0.

Q is most preferably a polar, amine functional residue of the formula —CH$_2$CH$_2$CH$_2$NHCH$_2$CH$_2$NH$_2$. In the formulae, "a" assumes values in the range from about 0 to about 2, "b" assumes values in the range from about 2 to about 3, "a"+"b" is less than or equal to 3, and "c" is a number in the range from about 1 to about 3. The molar ratio of the R$_a$Q$_b$SiO$_{(4-a-b)/2}$ units to the R$_c$SiO$_{(4-c)/2}$ units is in the range from about 1:2 to 1:65, preferably from about 1:5 to about 1:65 and most preferably from about 1:15 to about 1:20. If one or more silicones of the above formula are used, the different variable substituents in the above formula can be different in the different silicone components that are present in the silicone mixture.

Particularly preferred agents according to the invention are characterized in that they contain at least one amino functional silicone of the formula (Si-IIa):

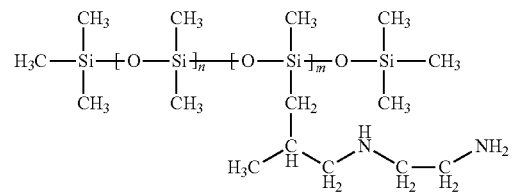

(Si-IIa)

wherein m and n are numbers the sum (m+n) of which is between 1 and 2000, preferably between 50 and 150, wherein n preferably assumes values of 0 to 1999 and in particular of 49 to 149 and m preferably assumes values of 1 to 2000, in particular of 1 to 10.

These silicones are referred to as trimethylsilylamodimethicones according to INCI nomenclature.

Particularly preferred are also agents according to the invention which contain an amino functional silicone of the formula (Si-IIb):

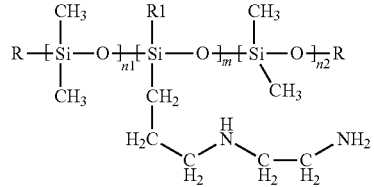

(Si-IIb)

wherein R denotes —OH, —O—CH$_3$ or a —CH$_3$ group and m, n1 and n2 are numbers, the sum (m+n1+n2) of which is between 1 and 2000, preferably between 50 and 150, the sum (n1+n2) preferably assuming values of 0 to 1999 and in particular of 49 to 149 and m preferably assuming values of 1 to 2000, in particular of 1 to 10.

These silicones are referred to as Amodimethicones according to the INCI nomenclature.

Preferred agents according to the invention are characterized in that they contain, based on their weight, 0.01 to 10 wt. %, preferably 0.1 to 8 wt. %, particularly preferably 0.25 to 7.5 wt. % and in particular 0.5 to 5 wt. % amino functional silicone(s).

The cyclic dimethicones, referred to in accordance with INCI as cyclomethicones, can also be used in accordance to the invention. Here, treatment agents are preferred that contain at least one silicone of the formula S1-III:

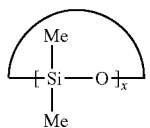 (Si-III)

wherein x denotes a number from 3 to 200, preferably from 3 to 10, more preferably from 3 to 7, and in particular 3, 4, 5 or 6.

Agents that are likewise preferred according to the invention are characterized in that they contain at least one silicone of the formula S1—IV:

$$R_3Si-[O-SiR_2]_x-(CH_2)_n-[O-SiR_2]_y-O-SiR_3 \quad (Si-IV)$$

wherein R denotes the same or different residues from the group —H, phenyl, benzyl, —CH$_2$—CH(CH$_3$)Ph, the C$_{1-20}$ alkyl residues, preferably —CH$_3$, —CH$_2$CH$_3$, —CH$_2$CH$_2$CH$_3$, —CH(CH$_3$)$_2$, —CH$_2$CH$_2$CH$_2$H$_3$, —CH$_2$CH(CH$_3$)$_2$, —CH(CH$_3$)CH$_2$CH$_3$, —C(CH$_3$)$_3$, x and y denote a number from 0 to 200, preferably from 0 to 10, more preferably from 0 to 7 and in particular 0, 1, 2, 3, 4, 5 or 6, and n denotes a number from 0 to 10, preferably from 1 to 8 and in particular 2, 3, 4, 5, 6.

For preference, the silicones are water-soluble. Preferred agents according to the invention are characterized in that they contain at least one water-soluble silicone.

For aesthetic reasons, "clear" products are often preferred by consumers. Preferred hair treatment agents according to the invention are therefore characterized in that they are transparent or translucent.

In the context of the present invention, transparent or translucent is understood to mean a composition having an NTU value of less than 100. The NTU value (Nephelometric Turbidity Unit; NTU) is a unit of turbidity measurements in liquids used in water treatment. It is the unit of the turbidity of a liquid measured with a calibrated nephelometer.

Furthermore in a preferred embodiment of the invention, an agent according to the invention can also contain UV filters. The UV filters to be used according to the invention are not subject to any general restrictions in terms of their structure and their physical properties. Rather, all UV filters that can be used in the cosmetics arts having an absorption maximum in the UVA (315-400 nm), UVB (280-315 nm) or UVC (<280 nm) range are suitable. UV filters with an absorption maximum in the UVB range, in particular in the range of about 280 to about 300 nm, are particularly preferred.

The UV filters used according to the invention can, for example, be selected from substituted benzophenones, p-aminobenzoic acid esters, diphenylacrylic acid esters, cinnamic acid esters, salicylic acid esters, benzimidazoles and o-aminobenzoic acid esters.

Those UV filters having a molar extinction coefficient at the absorption maximum greater than 15,000, in particular greater than 20,000, are preferred.

Furthermore it has been found that, with structurally similar UV filters, in many cases the water-insoluble compound has the greater action in the context of the teaching according to the invention compared with those water-soluble compounds that differ therefrom by one or more additional ionic groups. In the context of the invention, those UV filters that dissolve in water at 20° C. at a level of no more than 1 wt. %, in particular no more than 0.1 wt. %, are to be understood as water-insoluble. Furthermore, these compounds should be at least 0.1, in particular at least 1 wt. % soluble in conventional cosmetic oil components at room temperature. The use of water-insoluble UV filters can therefore be preferred according to the invention.

According to another embodiment of the invention, the UV filters bearing a cationic group, in particular a quaternary ammonium group, are preferred.

Two preferred UV filters with cationic groups are the commercially available compounds cinnamic acid amidopropyl trimethylammonium chloride (Incroquat®UV-283) and dodecyl dimethylaminobenzamidopropyl dimethylammonium tosylate (Escalol® HP 610).

Naturally, the present invention also contemplates the use of a combination of multiple UV filters. In the context of this embodiment, the combination of at least one water-insoluble UV filter with at least one UV filter having a cationic group is preferred.

The UV filters are contained in the agents according to the invention generally in quantities of 0.1-5 wt. %, based on the total agent. Quantities of 0.4-2.5 wt. % are preferred.

In addition, it may prove advantageous if penetration auxiliaries and/or swelling agents are contained in the agents according to the invention. These can include, for example, urea and urea derivatives, guanidine and derivatives thereof, arginine and derivatives thereof, water glass, imidazole and derivatives thereof, histidine and derivatives thereof, benzyl alcohol, glycerol, glycol and glycol ethers, propylene glycol and propylene glycol ethers, for example propylene glycol monoethyl ether, carbonates, hydrogen carbonates, diols and triols, and in particular 1,2-diols and 1,3-diols, such as for example 1,2-propanediol, 1,2-pentanediol, 1,2-hexanediol, 1,2-dodecanediol, 1,3-propanediol, 1,6-hexanediol, 1,5-pentanediol and 1,4-butanediol.

The present invention also provides a method for treating keratinic fibers, in particular human hair, with said method comprising the step of applying a hair treatment agent according to the invention onto keratinic fibers and either left there until the next hair wash or rinsed out after an exposure period of 30 to 300 seconds. The time in contact with the keratinic fibers is time sufficient to affect one or more properties of keratinic fibers.

With regard to preferred embodiments of the methods according to the invention, the statements relating to the agents according to the invention apply *mutatis mutandis*.

The present invention also provides the use of hair treatment agents according to the invention for improving at least one of the properties: tensile strength of keratinic fibers, in particular human hair; optical appearance, in particular gloss, of keratinic fibers, in particular human hair; stabilizing of the moisture balance of keratinic fibers, in particular human hair; combability of keratinic fibers, in particular human hair; delaying of the ageing process of keratinic fibers, in particular human hair; restructurability of keratinic fibers, in particular human hair, during and after the permanent wave process; reduction of the loss of elasticity of keratinic fibers, in particular human hair, when damaged by atmospheric effects; increase in the water repellency of the hair surface and "impregnation" of the hair.

With regard to preferred embodiments of the uses according to the invention, the statements relating to the agents according to the invention also apply *mutatis mutandis*.

EXAMPLES

In each of the exemplary embodiments below, ingredients are listed in weight percent wt. % based on the total weight of the hair treatment agent composition.

The ingredients in the exemplary embodiments are as follows:

Proteolipids:

Proteolipid A: (wheat protein)-O—C(O)—$(CH_2)_{10}$—$CH_3$;
Proteolipid B: (wheat protein)-O—C(O)—$(CH_2)_{16}$—$CH_3$;
Proteolipid C: (wheat protein)-$N^+(CH_3)_2$—$(CH_2)_{16}$—$CH_3$;
Proteolipid D: $H_3C$—$(CH_2)_{17}$—$N^+(CH_3)_2$—$CH_2$—CH(OH)—$CH_2$—(wheat protein);
Proteolipid E: $H_3C$—$(CH_2)_{17}$—$N^+(CH_3)_2$—$CH_2$—CH(OH)—$CH_2$—(wheat protein);
Proteolipid F: (wheat protein)-$N^+(CH_3)_2$—$CH_2$—CH(OH)—$CH_2$-cocoyl;
Proteolipid G: (keratin)-O—C(O)—$(CH_2)_{10}$—$CH_3$;
Proteolipid H: (keratin)-O—C(O)—$(CH_2)_{16}$—$CH_3$;
Proteolipid I: (keratin)-$N^+(CH_3)_2$—$(CH_2)_{16}$—$CH_3$;
Proteolipid J: $H_3C$—$(CH_2)_{17}$—$N^+(CH_3)_2$—$CH_2$—CH(OH)—$CH_2$-(keratin);
Proteolipid K: $H_3C$—$(CH_2)_{17}$—$N^+(CH_3)_2$—$CH_2$—CH(OH)—$CH_2$-(keratin); and,
Proteolipid L: (keratin)-$N^+(CH_3)_2$—$CH_2$—CH(OH)—$CH_2$-cocoyl.

Other Ingredients:

Euperlan® PK3000 approx. 60-64% solids; INCI name: Glycol Distearate, Glycerin, Laureth-4, Cocamidopropyl Betaine (Cognis);

Cetiol® HE coconut monoglyceride with approx. 7.3 EO units (INCI name: PEG-7 Glyceryl Cocoate) (Cognis);

Polymer JR® 400 quaternized hydroxyethyl cellulose (INCI name: Polyquaternium-10) (Amerchol);

Dehyquart® F75 fatty alcohols/methyl triethanol ammonium methyl sulfate dialkyl ester mixture (INCI name: Distearoylethyl Hydroxyethylmonium Methosulfate, Cetearyl Alcohol) (Henkel);

Varisoft®W 575 PG INCI name: Quaternium-87 (Goldschmidt);

Emulmetik® 100 Lecithin (Degussa);

Cutina® CP Cetyl palmitate (Cognis);

Dehyquart® A-CA trimethylhexadecylammonium chloride (approx. 24-26% actives) (INCI name: Water, Cetrimonium Chloride) (Cognis);

Gluadin® W20 wheat protein hydrolyzate (min. 20% solids; INCI name: Water, Hydrolyzed Wheat Protein, Sodium Benzoate, Phenoxyethanol, Methylparaben, Propylparaben) (Cognis);

Salcare® SC 96 approx. 50% actives; INCI name: Polyquatemium-37, Propylene Glycol Dicaprylate/Dicaprate, PPG-1 Trideceth-6 (CIBA);

Synthalen® K polyacrylic acid (approx. 89% active substance content; INCI name: Carbomer) (3V Sigma);

Neutrol® TE N,N,N',N'-tetrakis(2-hydroxypropyl)ethylenediamine (INCI name: Tetrahydroxypropyl Ethylenediamine) (BASF);

Luviskol® K30 polyvinylpyrrolidone (100% solids; INCI name: PVP) (BASF);

Gafquat® 755 dimethylaminoethyl methacrylate/vinylpyrrolidone copolymer, quaternized with diethyl sulfate (approx. 19% solids in water; INCI name: Polyquatemium-11) (ISP);

Dow Corning 1401®dimethyl cyclosiloxane/dimethyl polysiloxanol mixture (approx. 13% solids; INCI name. Cyclomethicone, Dimethiconol) (Dow Corning);

Sepigel® 305 approx. 45-49% solids; INCI name: Polyacrylamide, $C_{13-14}$ Isoparaffin, Laureth-7) (Seppic); and, Cutina® GMS-V glycerol mono-/dipalmitate/stearate (INCI name: Glyceryl Stearate) (Cognis).

Shampoo Compositions

| Shampoos | A | B | C | D | E | F |
| --- | --- | --- | --- | --- | --- | --- |
| Citric acid, anhydrous | 0.5 | 0.5 | 0.5 | 0.5 | 0.5 | 0.5 |
| Sodium lauryl ether sulfate 25% | 50 | 50 | 50 | 50 | 50 | 50 |
| Disodium Cocoamphodiacetate | 7 | 7 | 7 | 7 | 7 | 7 |
| Salicylic acid | 0.2 | 0.2 | 0.2 | 0.2 | 0.2 | 0.2 |
| D-Panthenol 75% | 0.5 | 0.5 | 0.5 | 0.5 | 0.5 | 0.5 |
| Na benzoate | 0.5 | 0.5 | 0.5 | 0.5 | 0.5 | 0.5 |
| Euperlan PK 3000 AM | 2 | 2 | 2 | 2 | 2 | 2 |
| Cetiol HE | 1 | 1 | 1 | 1 | 1 | 1 |
| Proteolipid A | 0.2 | — | — | — | — | — |
| Proteolipid B | — | 0.2 | — | — | — | — |
| Proteolipid C | — | — | 0.2 | — | — | — |
| Proteolipid D | — | — | — | 0.2 | — | — |
| Proteolipid E | — | — | — | — | 0.2 | — |
| Proteolipid F | — | — | — | — | — | 0.2 |
| Polymer JR 400 | 0.5 | 0.5 | 0.5 | 0.5 | 0.5 | 0.5 |
| Casein | 1.0 | 1.0 | 1.0 | 1.0 | 1.0 | 1.0 |
| Perfume | 0.5 | 0.5 | 0.5 | 0.5 | 0.5 | 0.5 |
| PEG-40 Hydrogenated Castor Oil 455 | 1 | 1 | 1 | 1 | 1 | 1 |
| Macadamia nut oil, refined | 0.2 | 0.2 | 0.2 | 0.2 | 0.2 | 0.2 |
| Sodium chloride fine-medium | 0.5 | 0.5 | 0.5 | 0.5 | 0.5 | 0.5 |
| Water, deionized | to 100 | to 100 | to 100 | to 100 | to 100 | to 100 |

In place of the proteolipids A to F used in the shampoo formulations above, 0.2 wt. % of one of the proteolipids G to L can be used in each case, while maintaining all of the properties of these shampoos.

Restructuring Creams

| Restructuring creams | A | B | C | D | E | F |
| --- | --- | --- | --- | --- | --- | --- |
| Paraffinum Liquidum | 1 | 1 | 1 | 1 | 1 | 1 |
| Dehyquait F 75 | 2 | 2 | 2 | 2 | 2 | 2 |
| Proteolipid A | 1.0 | — | — | — | — | — |
| Proteolipid B | — | 1.0 | — | — | — | — |
| Proteolipid C | — | — | 1.0 | — | — | — |
| Proteolipid D | — | — | — | 1.0 | — | — |
| Proteolipid E | — | — | — | — | 1.0 | — |
| Proteolipid F | — | — | — | — | — | 1.0 |
| Varisoft W 75 PG | 1.5 | 1.5 | 1.5 | 1.5 | 1.5 | 1.5 |
| Cetearyl Alcohol | 3.5 | 3.5 | 3.5 | 3.5 | 3.5 | 3.5 |
| Emulmetik 100 | 0.4 | 0.4 | 0.4 | 0.4 | 0.4 | 0.4 |
| Propylparaben | 0.15 | 0.15 | 0.15 | 0.15 | 0.15 | 0.15 |
| Cutina CP | 0.7 | 0.7 | 0.7 | 0.7 | 0.7 | 0.7 |
| Stearamidopropyl dimethylamine | 1 | 1 | 1 | 1 | 1 | 1 |
| Dehyquart A CA | 3 | 3 | 3 | 3 | 3 | 3 |
| Citric acid | 0.5 | 0.5 | 0.5 | 0.5 | 0.5 | 0.5 |
| Methylparaben | 0.15 | 0.15 | 0.15 | 0.15 | 0.15 | 0.15 |
| Phenoxyethanol, pure | 0.4 | 0.4 | 0.4 | 0.4 | 0.4 | 0.4 |
| D-Panthenol 75% | 0.2 | 0.2 | 0.2 | 0.2 | 0.2 | 0.2 |
| Gluadin W 20 | 1 | 1 | 1 | 1 | 1 | 1 |
| Perfume | 0.4 | 0.4 | 0.4 | 0.4 | 0.4 | 0.4 |
| Salcare SC 96 | 1 | 1 | 1 | 1 | 1 | 1 |
| Water, deionized | to 100 | to 100 | to 100 | to 100 | to 100 | to 100 |

In place of the proteolipids A to F used in the restructuring cream formulations above, 0.2 wt. % of one of the proteolipids G to L can be used in each case, while maintaining all of the properties of these restructuring creams.

Leave-in Treatments

| Leave in Treatments | A | B | C | D | E | F |
| --- | --- | --- | --- | --- | --- | --- |
| Synthalen K | 0.25 | 0.25 | 0.25 | 0.25 | 0.25 | 0.25 |
| Sepigel 305 | 1 | 1 | 1 | 1 | 1 | 1 |
| Dehyquart F 75 | 0.5 | 0.5 | 0.5 | 0.5 | 0.5 | 0.5 |
| Polymer JR 400 | 0.3 | 0.3 | 0.3 | 0.3 | 0.3 | 0.3 |
| Neutral TE | 0.4 | 0.4 | 0.4 | 0.4 | 0.4 | 0.4 |
| Proteolipid A | 0.75 | — | — | — | — | — |
| Proteolipid B | — | 0.75 | — | — | — | — |
| Proteolipid C | — | — | 0.75 | — | — | — |
| Proteolipid D | — | — | — | 0.75 | — | — |
| Proteolipid E | — | — | — | — | 0.75 | — |
| Proteolipid F | — | — | — | — | — | 0.75 |
| Perfume | 0.3 | 0.3 | 0.3 | 0.3 | 0.3 | 0.3 |
| D-Panthenol 75% | 0.5 | 0.5 | 0.5 | 0.5 | 0.5 | 0.5 |
| Luviskol K 30 powder | 0.5 | 0.5 | 0.5 | 0.5 | 0.5 | 0.5 |
| Gafquat 755N | 0.5 | 0.5 | 0.5 | 0.5 | 0.5 | 0.5 |
| Dow Corning 1401 Fluid | 1 | 1 | 1 | 1 | 1 | 1 |
| Ethanol 96% DEP denatured | 15 | 15 | 15 | 15 | 15 | 15 |
| Sepigel 305 | 1.6 | 1.6 | 1.6 | 1.6 | 1.6 | 1.6 |
| Water, deionized | to 100 | to 100 | to 100 | to 100 | to 100 | to 100 |

In place of the proteolipids A to F used in the leave-in treatment formulations above, 0.2 wt. % of one of the proteolipids G to L can be used in each case, while maintaining all of the properties of these leave-in treatments.

Intensive Conditioner

| Intensive conditioner | A | B | C | D | E | F |
| --- | --- | --- | --- | --- | --- | --- |
| Varisoft W 75 PG | 1.5 | 1.5 | 1.5 | 1.5 | 1.5 | 1.5 |
| Paraffinum Liquidum | 1 | 1 | 1 | 1 | 1 | 1 |
| Dehyquart F 75 | 2 | 2 | 2 | 2 | 2 | 2 |
| Stearamidopropyl dimethylamine | 1 | 1 | 1 | 1 | 1 | 1 |
| Proteolipid A | 1.5 | — | — | — | — | — |
| Proteolipid B | — | 1.5 | — | — | — | — |
| Proteolipid C | — | — | 1.5 | — | — | — |
| Proteolipid D | — | — | — | 1.5 | — | — |
| Proteolipid E | — | — | — | — | 1.5 | — |

-continued

| Intensive conditioner | A | B | C | D | E | F |
|---|---|---|---|---|---|---|
| Proteolipid F | — | — | — | — | — | 1.5 |
| Cetearyl Alcohol | 5 | 5 | 5 | 5 | 5 | 5 |
| Cutina GMS-V | 1 | 1 | 1 | 1 | 1 | 1 |
| Citric acid | 0.3 | 0.3 | 0.3 | 0.3 | 0.3 | 0.3 |
| Dehyquart A CA | 5 | 5 | 5 | 5 | 5 | 5 |
| Salcare SC 96 | 0.5 | 0.5 | 0.5 | 0.5 | 0.5 | 0.5 |
| Perfume | 0.4 | 0.4 | 0.4 | 0.4 | 0.4 | 0.4 |
| D-Panthenol 75% | 0.5 | 0.5 | 0.5 | 0.5 | 0.5 | 0.5 |
| Water, deionized | to 100 | to 100 | to 100 | to 100 | to 100 | to 100 |

In place of the proteolipids A to F used in the intensive conditioner formulations above, 0.2 wt. % of one of the proteolipids G to L can be used in each case, while maintaining all of the properties of these intensive conditioners.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

We claim:

1. A hair treatment agent comprising:
   a. at least one surfactant; and
   b. at least one proteolipid of formula (I), $$R'—X—R''  \qquad (I)$$

wherein R' denotes a straight-chained or branched, saturated or unsaturated hydrocarbon residue with 11 to 24 carbon atoms; R'' denotes a protein, a peptide, or a protein hydrolyzate and further includes at least one Leu-Tyr-Glu-Glu-Glu-Ile-Arg-Val-Leu amino acid sequence; X denotes $—N^+(R^{III}{}_2)R^{IV}—$, or $—N(R^{III})R^{IV}—$; $R^{III}$ is $—(CH_2)_x—CH_3$ with x=0-22; and $R^{IV}$ is $—CH_2—$, $CH(OH)—CH_2—$, or $—(CH_2)_x—$ with x=0-22.

2. The agent of claim 1, wherein said surfactant is selected from the group consisting of anionic surfactants, nonionic surfactants, cationic surfactants, amphoteric surfactants, and mixtures thereof.

3. The agent of claim 1, wherein said surfactant is present from 0.5 to 70 wt. %, based on the total weight of the agent.

4. The agent of claim 3, wherein said surfactant is present from 5 to 25 wt. %, based on the total weight of the agent.

5. The agent of claim 4, wherein said surfactant comprises 5 to 15 wt. % of a fatty alcohol ether sulfate having the general formula:

$$H_3C—(CH_2)_n—(OCH_2CH_2)_k—OSO_3{}^-M^+$$

wherein n is 5 to 21; k is 1-10; and M is a cation selected from the group consisting of $Na^+$, $K^+NH_4{}^+$, $½Mg^{2+}$, $½Zn^{2+}$, and mixtures thereof.

6. The agent of claim 1, wherein said proteolipid is present from 0.01 to 10 wt. %, based on the total weight of the agent.

7. The agent of claim 1, wherein R'' is keratin or a keratin hydrolyzate.

8. A hair treatment agent comprising:
   a. at least one surfactant; and
   b. at least one proteolipid of formula (I), $$R'—X—R'' \qquad (I)$$

wherein R'' denotes a protein, a peptide, or a protein hydrolyzate, X is $—N^+(CH_3)_2—CH_2—CH(OH)—CH_2—$ and R' is $—(CH_2)_{17}—CH_3$.

9. The agent of claim 1, wherein $R^{III}$ is $—CH_3$ and $R^{IV}$ is $—(CH_2)_x—$ with x=0, 1, 2, 3, 4, 5, 6, 7, or 8.

10. The agent of claim 1, further comprising a protein hydrolyzate at a level of 0.01 to 10 wt. %, based on the total weight of the agent.

11. The agent of claim 10, wherein said protein hydrolyzate is a keratin hydrolyzate, present at a level of 0.5 to 2.0 wt. %, based on the total weight of the agent.

12. The agent of claim 8, wherein said surfactant is selected from the group consisting of anionic surfactants, nonionic surfactants, cationic surfactants, amphoteric surfactants, and mixtures thereof.

13. The agent of claim 8, wherein said surfactant is present from 0.5 to 70 wt. %, based on the total weight of the agent.

14. The agent of claim 13, wherein said surfactant is present from 5 to 25 wt. %, based on the total weight of the agent.

15. The agent of claim 14, wherein said surfactant comprises 5 to 15 wt. % of a fatty alcohol ether sulfate having the general formula:

$$H_3C—(CH_2)_n—(OCH_2CH_2)_k—OSO_3{}^-M^+$$

wherein n is 5 to 21; k is 1-10; and M is a cation selected from the group consisting of $Na^+$, $K^+NH_4{}^+$, $½Mg^{2+}$, $½Zn^{2+}$, and mixtures thereof.

16. The agent of claim 8, wherein $R^{III}$ is $—CH_3$ and $R^{IV}$ is $—(CH_2)_x—$ with x=0, 1, 2, 3, 4, 5, 6, 7, or 8.

17. The agent of claim 8, further comprising a protein hydrolyzate at a level of 0.01 to 10 wt. %, based on the total weight of the agent.

18. The agent of claim 17, wherein said protein hydrolyzate is a keratin hydrolyzate, present at a level of 0.5 to 2.0 wt. %, based on the total weight of the agent.

* * * * *